United States Patent [19]
Palti

[11] Patent Number: 5,190,041
[45] Date of Patent: Mar. 2, 1993

[54] SYSTEM FOR MONITORING AND CONTROLLING BLOOD GLUCOSE

[76] Inventor: Yoram Palti, 51 Ruth Street, Haifa 34404, Israel

[21] Appl. No.: 816,303

[22] Filed: Dec. 27, 1991

Related U.S. Application Data

[62] Division of Ser. No. 392,828, Aug. 11, 1989, Pat. No. 5,101,814.

[51] Int. Cl.⁵ .......................... A61F 2/02; A61F 2/48; A61F 2/70; A61B 5/05
[52] U.S. Cl. .................................. 128/635; 128/632; 128/633; 604/50; 604/66; 623/24; 623/25; 424/422; 424/423; 424/451; 424/556; 424/571; 436/151; 514/866
[58] Field of Search ............... 424/422, 423, 556, 571; 436/151; 514/866; 128/632, 633, 635; 604/50, 66; 623/24, 25

[56] References Cited

U.S. PATENT DOCUMENTS

| | | | |
|---|---|---|---|
| 4,136,101 | 1/1979 | Kazan | 544/260 |
| 4,332,893 | 6/1982 | Rosenberg | 435/68 |
| 4,352,883 | 10/1982 | Lim | 435/178 |
| 4,353,888 | 10/1982 | Sefton | 424/25 |
| 4,374,987 | 2/1983 | Singh et al. | 544/260 |
| 4,375,987 | 3/1983 | Lange et al. | 106/95 |
| 4,409,331 | 10/1983 | Lim | 435/178 |
| 4,436,094 | 3/1984 | Cerami | 128/635 |
| 4,633,878 | 1/1987 | Bombardieri | 128/635 |
| 4,663,286 | 5/1987 | Tsang | 435/174 |
| 4,689,293 | 8/1987 | Goosen et al. | 435/1 |
| 4,703,756 | 11/1987 | Gough et al. | 128/635 |
| 4,704,029 | 11/1987 | Van Heuvelen | 128/633 |
| 4,798,786 | 1/1989 | Tice et al. | 435/177 |
| 4,803,168 | 2/1989 | Jarvis | 435/178 |
| 4,822,336 | 2/1992 | DiTraglia | 604/50 |
| 4,919,141 | 4/1990 | Zier et al. | 128/635 |

FOREIGN PATENT DOCUMENTS 62-213760  3/1986  Japan.

OTHER PUBLICATIONS

Akaike, N. et al, "Electrical Responses of Frog Taste Cells To Chemical Stimuli", J. Physiol. (1976), 254, pp. 87-107.

Altman, J. et al, "Long-Term Plasma Glucose Normalization In Experimental Diabetic Rats With Macroencapsulated Implants Of Benign Human Insulinomas", Diabetes, vol. 35, Jun. 1986.

Amsterdam, A. et a, "Structural and Functional Characterization of Isolated Pancreatic Exocrine Cells", Proc. Nat. Acad. Sci. USA, vol. 69, No. 10, pp. 3028-3032, Oct. 1972.

Amsterdam, A. et al, "Studies On Dispersed Pancreatic Exocrine Cells", Journal of Cell Biology, vol. 63, (1974) pp. 1037-1056.

Atwater, I. et al, "Three K Channels in Human Pancreatic B-Cells Identical to Those in Rat B-Cells", Biophysical Journal, M-AM-A9, vol. 55, (1989).

Avenet, P. et al, "Patch-Clamp Study of Isolated Taste Receptor Cells of the Frog", J. Membrane Biol. 97, pp. 223-240 (1987).

Brown, J. et al, "Fetal Pancreas Transplantation for Reversal of Streptozotocin-induced Diabetes in Rats", Diabetes, vol. 25, No. 1, pp. 56-64.

Carrington, C. A. et al "Five New Insulin-Producing Cell Lines With Differing Secretory Properties", J. Endocr. (1986) 109, pp. 193-200.

(List continued on next page.)

*Primary Examiner*—Thurman K. Page
*Assistant Examiner*—Carlos Azpuru
*Attorney, Agent, or Firm*—Bryan Cave

[57] ABSTRACT

Systems are disclosed which utilize implanted glucose sensitive living cells to monitor blood glucose levels. The implanted cells produce a detectable electrical or optical signal in response to changes in glucose concentration in surrounding tissue. The signal is then detected and interpreted to give a reading indicative of blood glucose levels. Capsules containing glucose sensitive cells and electrodes for detecting electrical activity are also disclosed. Method of monitoring blood glucose are also described utilizing the systems and capsules disclosed.

16 Claims, 8 Drawing Sheets

OTHER PUBLICATIONS

Charles, R. et al "A Multi-Center Study of the Laserdish Electrode", Cardiac Pacing and Electrophysiology, Proceedings of the VIIIth World Symposium on Cardiac Pacing and Electrophysiology, Jun. 7–11, 1987.

Eddlestone, G. T. et al "Electrical Coupling Between Cells in Islets of Langerhans From Mouse", J. Membrane Biol. 77, pp. 1–14, (1984).

Grinvald, A. et al "Optical Imaging of Neuronal Activity" Physiological Review, vol. 68, No. 4, Oct. 1988.

Gross, David et al "Optical Imaging of Cell Membrane Potential Changes Induced by Applied Electric Fields" Biophysical Journal, vol. 50, pp. 339–348 (1986).

Hidalgo, J. et al "Calcium Currents in Rat Pancreatic B-Cells in Culture", Biophysical Journal, W-PM-A3 vol. 55, (1989).

Howard, R. B. et al "The Enzymatic Preparation of Isolated Intact Parenchymal Cells From Rat Liver", The Journal of Cell Biology, vol. 35, pp. 675–684 (1967).

Meda, P. et al "The Topography of Electrical Synchrony Among B-Cells in the Mouse of Langerhans", Quarterly Journal of Experimental Physiology (1984) 69, pp. 719–735.

Palade, G. E. et al "Structure, Chemistry and Function of the Pancreatic Exocrine Cell".

Pressel, D. et al "Ion Channel Currents in Canine Pancreatic Islet B Cells", Biophysical Journal, W-Pos 221, vol. 55, (1989).

Ricordi, C. et al "A Method for the Mass Isolation of Islets From the Adult Pig Pancreas", Diabetes, vol. 35 (Jun. 1986).

Scott, A. M. et al "A Method for the Simultaneous Measurement of Insulin Release and B Cell Membrane Potential in Single Mouse Islets of Langerhans", Diabetologia (1981) 21:470–475.

Sorenson, R. L. et al "Dissociation of Glucose Stimulation of Somatostatin and Insulin Release From Glucose Inhibition of Glucagon Release in the Isolated Perfused Rat Pancreas", Diabetes, vol. 32 (Jun. 1983).

Schmidt, R. E. et al "The Effect of Pancreatic Islet Transplantation and Insulin Therapy on Experimental Diabetic Autonomic Neuropathy", Diabetes, vol. 32, (Jun. 1983).

Tonosaki K. et al "Voltage-and Current-Clamp Recordings of the Receptor Potential in Mouse Taste Cell", Brain Research, 445 (1988) pp. 363–366.

Winkle, R. A. et al "Comparison of Defibrillation Efficacy in Humans Using a New Catheter and Superior Vena Cava Spring-Left Ventricular Patch Electrodes", JACC, vol. 11, No. 2, Feb. 1988:365–70.

SYSTEM FOR MONITORING AND CONTROLLING BLOOD GLUCOSE

This is a divisional of U.S. application Ser. No. 07/392,828, filed Aug. 11, 1989, now U.S. Pat. No. 5,101,814.

FIELD OF THE INVENTION

The present invention relates to means for monitoring the level of glucose in blood and bodily tissues Particularly, the invention relates to a system for monitoring glucose with glucose sensitive cells that produce an electrical response to glucose levels in their surrounding medium which is then used to determine the blood glucose level, to administer insulin or to take other measures to alter the blood glucose level such as diet adjustment.

BACKGROUND OF THE INVENTION

Diabetes is a metabollic disorder that afflicts tens of millions of people in the developed countries of the world, with many millions more probably affected in underdeveloped nations. Diabetes results from the inability of the body to properly utilize and metabolize carbohydrates, particularly glucose. Normally, the finely-tuned balance between glucose in the blood and glucose in bodily tissue cells is maintained by insulin, a hormone produced by the pancreas which controls, among other things, the transfer of glucose from blood into body tissue cells. .Upsetting this balance causes many complications and pathologies including heart disease, coronary and peripheral artery sclerosis, peripheral neuropathies, retinal damage, cataracts, hypertension and coma and death from hypoglycemic shock.

In patients with insulin-dependent diabetes, the symptoms of the disease can be controlled by administering additional insulin (or other agents that have similar effects) by injection or by external or implantable insulin pumps The "correct" insulin dosage is a function of the level of glucose in the blood. Ideally, insulin administration should be continuously readjusted in response to changes in blood glucose level. However, at present, blood glucose levels can only be determined directly by a blood sample Unfortunately, since drawing the sample is invasive, blood glucose is usually only determined once daily or less often. As a result, insulin dosage is not optimally coordinated with blood glucose levels and complications can continue to be manifested. It would, therefore, be desirable to provide non-invasive means for more closely monitoring blood glucose levels and coordinating insulin dosages with such levels.

Many attempts have been made to develop a reliable less invasive or non-invasive way to measure blood glucose level. One of the most widely used methods has been measurement of glucose excreted in the urine, which is under certain conditions an indicator of blood glucose concentration In its most convenient form, a "dipstick", which has been coated with chemical reagents, is dipped into a urine sample. Glucose in the urine then reacts with the chemical reagents on the dipstick to produce a color change which corresponds to the appropriate range of concentration. The level of urine glucose is then correlated with blood levels on the basis of statistical data and previous experience with the specific patient. However, urine testing has presented several drawbacks. Foremost, is the tenuous link between urine glucose level and blood glucose levels. Although general trends in blood levels within a certain range are usually reflected in urine levels, moderate or periodic fluctuations of blood levels may not be reflected in urine content. Therefore, any dosage change made on the basis of urine analysis is not finely-tuned to blood levels Furthermore, other substances in urine can cause inaccuracy in measurement by interfering with chemical reactions necessary to produce the color change on the dipstick. Finally, like blood sampling, urine analysis can only be performed at relatively widely spaced intervals when the patient produces urine for analysis.

Other systems have been proposed for monitoring blood glucose levels by implanting a glucose sensitive probe into the patient. Such probes have measured various properties of blood or other tissues, including optical absorption, electrochemical potential and enzymatic products U.S. Pat. Nos. 4,436,094 and 4,704,029 disclose two examples of blood glucose level probes. U.S. Pat. No. 4,436,094 utilizes an implantable electrode which contains a charged carbohydrate species which, in the absence of glucose, is bound to a component of the electrode and does not affect the potential measured by the electrode. In the presence of glucose, however, charged carbohydrate is displaced from the binding component by molecules of glucose, and as a result of its charge, affects the potential measurement by the electrode The measured potential can then be correlated to the concentration of glucose.

U.S. Pat. No. 4,704,029 discloses an implantable glucose monitor that utilizes a refractometer which measures the index of refraction of blood adjacent to an interface with the transparent surface of the refractometer by directing laser light at the interface to measure the index of refraction of the blood by the amount of radiation reflected at the interface. As the blood glucose concentration increases, the index of refraction of blood increases. By comparing the intensity of the light reflected by the blood with the intensity of light before contact in the blood, glucose concentration can be determined.

Another approach to tying blood glucose levels to insulin dosage has centered around the implantation of pancreatic cells which produce insulin in response to changes in blood glucose levels as shown for example in Altman et al., Diabetes 35:625-633 (1986); Recordi et al., Diabetes 35:649-653 (1986); Amsterdam et al., J. Cell Biol. 63:1037-1056 (1974); Brown et al , Diabetes 25:56-64 (1976); Carrington et al., J. Endocr. 109:193-200 (1986); and Sonerson et al , Diabetes 32 561-567 (1983) Altman et al. were able to maintain normal blood glucose levels in diabetic mice by implanting cells (1) in areas impermeable to antibodies, (2) suppressing the immunogenecity of the implantable cells in tissue culture before the implantation and (3) enclosing the cells in a capsule that was impermeable to antibodies. However, the implantation methods of Altman et al. and others are severely limited by the availability of large enough masses of cells for effective implantation by the ability to reliably get insulin production over extended periods after implantation.

SUMMARY OF THE INVENTION

In accordance with the present invention, systems are disclosed which utilize implanted glucose sensitive living cells to monitor blood glucose levels by monitoring glucose levels in bodily tissues in which the glucose level is in equilibrium with that of the blood. In this respect, the implanted cells are similarly situated to endogenous insulin secreting glucose sensitive cells. The implanted cells produce a detectable electrical or optical signal in response to changes in glucose concentration in surrounding tissue The signal is then detected and interpreted to give a reading indicative of blood glucose levels. This reading can then be used as a basis for altering insulin or other drug dosage for injection, as a basis for giving instructions to an external implanted insulin pump to alter the amount of insulin delivered by the pump, or as a basis for taking other corrective measures, such as altering diet. As a result, blood sugar levels can be more closely monitored and controlled in a noninvasive way and insulin dosage can be more closely tailored with concomitant control of symptoms associated with diabetes.

A system for monitoring tissue and blood glucose level is disclosed which comprises glucose sensitive cells which are capable of producing a signal in response to changes in glucose concentration in the medium surrounding the cells. The signal produced can either be electrical or optical. In certain embodiments, the cells are contained in a capsule which is constructed from a membrane or similar substance which is impermeable to antibodies, yet permeable to nutrients to keep the cells alive. The capsule can also be fitted with means for collecting the signals produced by the cells.

In instances where the signal is electrical, these collecting means can be metal electrodes which are placed in contact with the cells such that the signal produced by the cells can be measured as a potential difference between the electrodes. The system can further include an implanted signal pickup device which is connected to the electrodes in the capsule for processing (e.g., amplifying and modulating) the signal for later transmission through the body surface, such as the skin, or for transmission to an external or implanted insulin pump. Once the signal is processed the pickup device passes the signal on to means for transmitting the processed signal In other embodiments, the implanted cells produce an electrical signal which can be detected by external electrodes without employing electrodes in the capsule or an implantable signal pick-up device.

In instances where the signal is optical, the signal is produced by a change in the optical qualities of the cells or specifically the membranes of the implanted cells. Preferably, the signal is produced by dyes contained within or coated on cellular membranes which will change the optical properties of the cells in response to changes in electrical activity of the cell. This change in optical quality can be detected through relatively transparent body surfaces, such as thin skin layers or fingernails. Alternatively, the optical change can be measured by an implanted optical detector which processes the detected signal much as the implanted pick-up device previously described processes electrical signals. The processed signal can be used to control an insulin pump or transmitted through the skin for external detection.

The electrical signal or the optical signal are detected through the skin by an external sensor and then correlated to a corresponding blood glucose level. The sensor includes means for detecting the signal, means for processing such signal and correlating it to the corresponding blood glucose level, and output means for reporting or relating the blood glucose level as determined.

Alternatively, the implanted signal pickup device can pass a processed signal on to an implanted insulin pump, which, in response to such signal, delivers an appropriate dosage of insulin corresponding to the determined blood glucose level.

Capsules for use in practicing the present invention are also disclosed which comprise a membrane which is impermeable to antibodies and is permeable to nutrients necessary for cell growth. Glucose sensitive cells are enclosed within the membrane, along with electrodes in contact with the cells such that changes in the electrical activity of the cells can be detected as a potential difference between the electrodes.

Alternatively, in place of the electrodes, the capsules can enclose means for "shorting-out" the interior of the capsule with respect to the exterior of the capsule such that the electrical activity of the cells is optimally dissipated on the exterior of the capsule. As a result, the electrical activity will be maintained at a level which can be detected by appropriate sensing means.

Capsules are also disclosed which contain glucose sensitive cells which have been treated such that the cellular membranes of the cells are coated with dyes which are sensitive to change in cellular membrane potential.

Finally, methods of monitoring the blood glucose level employing the capsules and systems of the present invention are disclosed. Basically, those methods comprise implanting into the patient glucose sensitive cells, detecting the signal produced by the cells in response to levels and/or changes in glucose concentration and correlating that signal with the corresponding blood glucose level. Methods of administering glucose are also disclosed which comprise administering a level of insulin (or other correcting agent) appropriate to the blood glucose level determined in accordance with the methods disclosed herein. Such insulin can be either administered manually or by operation of an external or implanted insulin pump which is connected to the detecting and monitoring system. It is understood that other therapeutic agents which will alter blood glucose levels, such as those sold under the tradenames "Dia Beta" (glyburide; Hoechst -Roussel), "Glucontrol" (glipizide; Pfizer) and "Diabinese" (chlorpropamide; Pfizer), can be substituted for insulin as described herein.

DETAILED DESCRIPTION OF THE INVENTION

Figure 1:
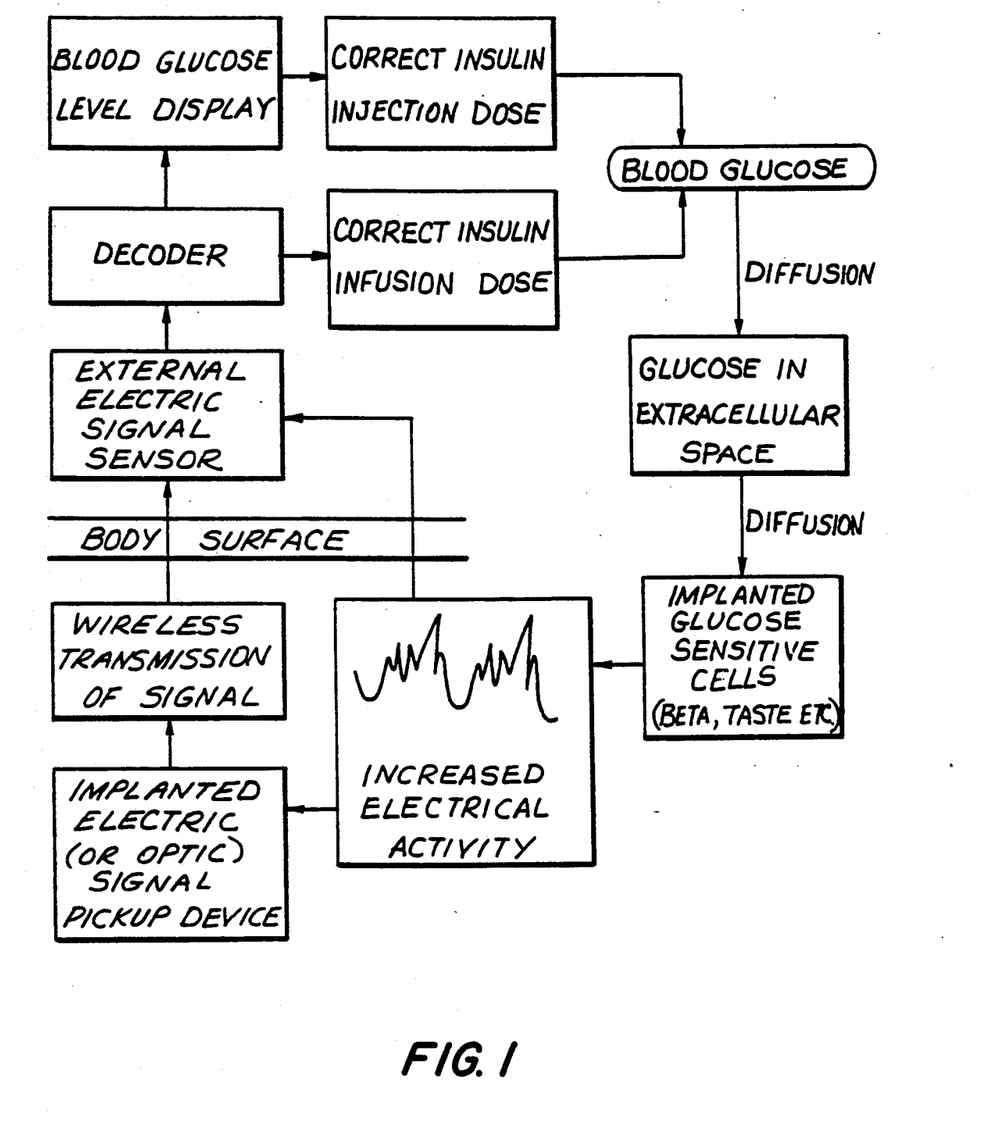
FIG. 1 is a schematic representation of the components and operation of a system of the present invention.
Figure 2A:
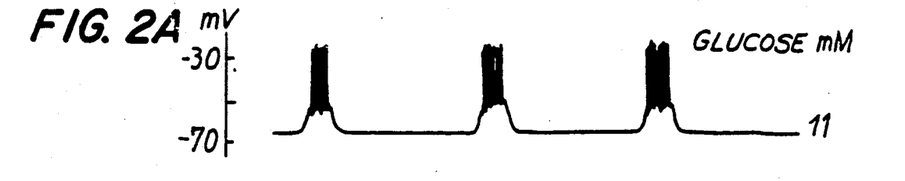
FIG. 2 depicts bursts of spiked electrical activity produced by pancreatic beta cells in response to various glucose concentrations.
Figure 2B:
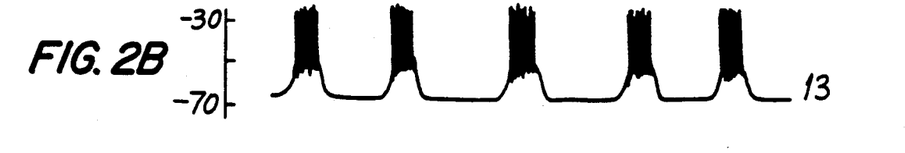
Figure 2C:
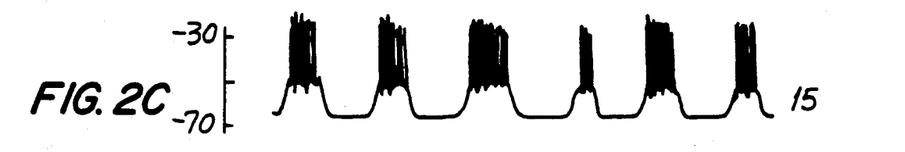
Figure 2D:
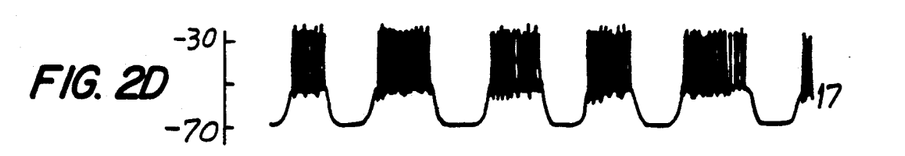
Figure 2E:
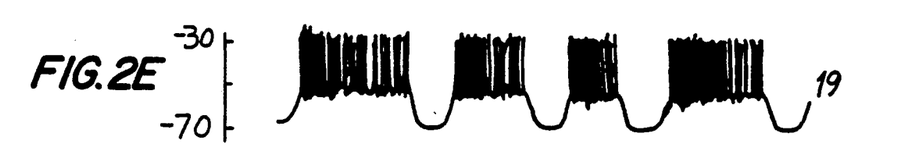
Figure 2F:
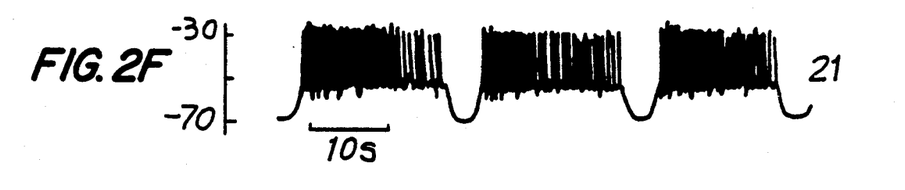
Figure 3A:
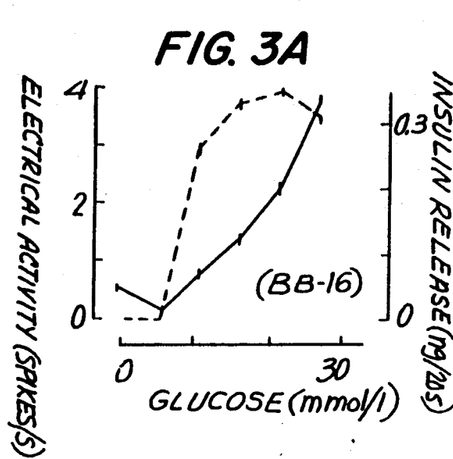
FIG. 3 contains graphs of electrical activity of six different preparations of beta cells in response to varying glucose concentration.
Figure 3B:
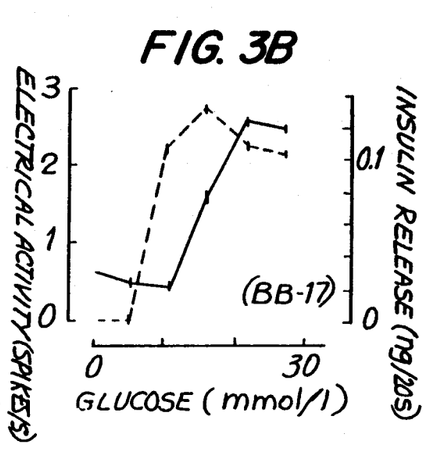
Figure 3C:
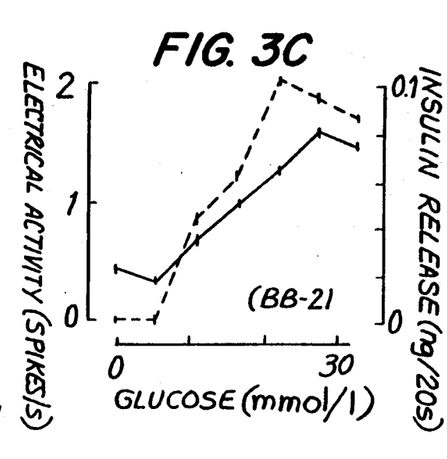
Figure 3D:
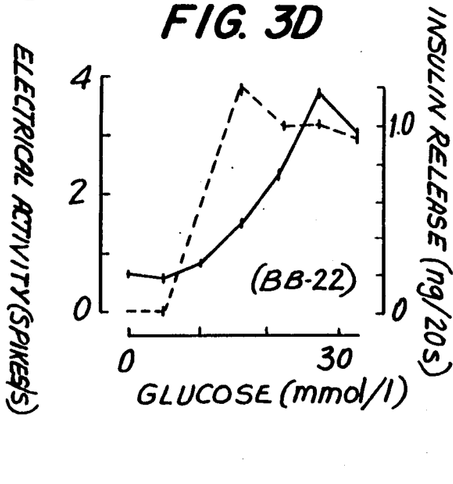
Figure 3E:
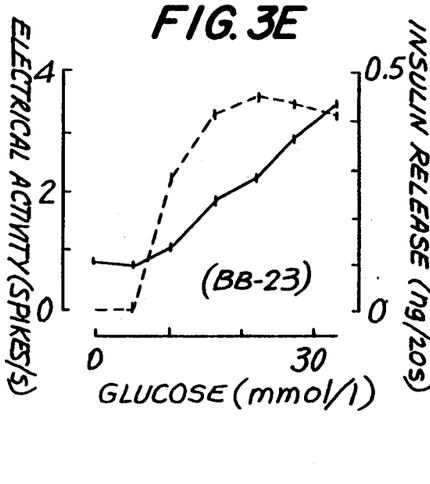
Figure 3F:
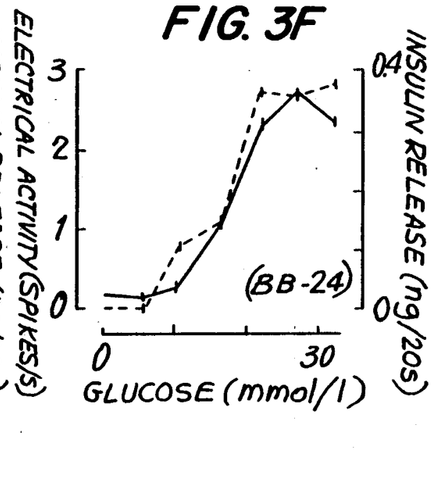

FIG. 1 schematically describes one embodiment of a system of the present invention which is described in further detail below. As shown at the upper right of FIG. 1, glucose diffuses from the bloodstream into the extracellular space in bodily tissues. Eventually the glucose diffuses to implanted glucose sensitive cells which are a part of the system of the present invention. The implanted cells respond by exhibiting electrical activity, such as a change in membrane potential, commensurate with the concentration of glucose in the extracellular space.

The electrical activity can be detected or monitored in one of two ways. Where the electrical activity is strong enough to be detected through a body surface (e.g., layers of skin), the electrical activity is detected directly by an external signal sensor. Alternatively, the electrical activity is monitored by an implanted signal pickup device. The pickup device processes and amplifies the electrical activity The amplified signal is then transmitted through a body surface (such as the skin) and is detected by the external signal sensor.

The external signal sensor contains or is connected to a decoder or microprocessor that interprets the signal. The decoder correlates the signal with blood glucose concentration on the basis of an algorithm and programmed information relating to the correlation between blood glucose levels and glucose levels at the implantation site for the patient in which the system is implanted. For example, the microprocessor can be programmed to correlate a glucose concentration of 20MM at the implantation site with a concentration of 22MM in the blood on the basis of prior and periodic blood sampling. Once the signal has been correlated and translated into a reading of the blood glucose concentration, the concentration information is used in one of two ways. First, the information can be displayed for reading by the patient or a person caring for the patient. On the basis of the displayed concentration, the correct insulin dose can be administered or diet can be adjusted. Alternatively, the concentration information is fed into an insulin pump, external or implanted, that infuses the correct insulin dosage on the basis of the determined blood glucose level. The concentration information can also be fed to other devices (such as automatic liquid feeding apparatus) which will take corrective action on the basis of such information.

The systems of the present invention utilize glucose sensitive living cells as sensors of the blood sugar levels either directly (by implantation in the bloodstream) or indirectly (by implantation in tissues in equilibrium with blood glucose levels) Any cell type that produces a detectable electrical activity in response to changes in glucose concentration in the surrounding environment can be used in practicing the present invention.

Beta cells from the islets of Langerhans in the pancreas are preferred glucose sensitive cells. Beta cells have been shown to produce electrical activity, action potentials, in response to glucose concentration and have the advantage that they respond properly to glucose in the concentration range relevant to patient monitoring. Scott et al., Diabetologia 21:470-475(1981); Pressel et al., Biophys. J. 55:540a (1989); Hidalgo et al., Biophys. J. 55:436a (1989); Atwater et al., Biophys. J. 55:7a (1980). Beta cells respond to glucose in bursts of spikes of electrical activity. The spike frequency, burst duration and pauses between bursts are all functions of glucose concentration. FIGS. 2 and 3 present data relating to the electrical activity of beta cells. As shown in FIG. 2, the burst duration increases as glucose concentration increases. The pause between bursts also decreases as glucose concentration increases In FIG. 3, the spike frequency (spikes/second) increases as glucose concentration increases. Each of these parameters (burst duration, pause duration and spike frequency), as well as spike shape, can be monitored alone or in combination as a source of signal corresponding to cellular electrical activity. It has also been established that the beta cells are electrically coupled, resulting in synchronized electrical activity of the cells. Eddlestone et al., J. Membrane Biol. 77:1-141 (1984), Meda et al., Quarterly J. Exper. Physiol. 69:719-735 (1984). Therefore, in response to a change in the glucose concentration, many cells fire their action potentials or electric signals in synchrony, producing a significantly amplified signal which is easier to detect.

Methods for isolating beta cells are described in the references cited in the preceding paragraph and in Amsterdam et al., J. Cell Biol. 63:1037-1056 (1979); Ricordi et al., Diabetes 35:649-653 (1986); and Carrington et al., J. Endocr. 109:193-200 (1986). In addition, any other method for isolating beta cells can be used which preserves the ability of the isolated cells to respond to changes in glucose concentration Other methods for culturing pancreatic cells are disclosed in Amsterdam et al, J. Cell Biol. 63 1037-1073 (1974); Amsterdam et al., Proc. Natl. Acad. Sci. USA 69: 3028-3032 (1972); Ciba Foundation Symposium on the Exocrine Pancreas, Reuck and Cameron, ed., p. 23-49 (J. and A. Churchill Ltd., London 1962); and Howard et al., J. Cell Biol. 35 675-684 (1967).

Sensory cells in taste buds have also been shown to respond to fluctuations in glucose concentration Ozeki, J. Gen. Physiol. 58:688-699 (1971); Avenet et al., J. Membrane Biol. 97:223-240 (1987); TonoSaki et al.; Brain Research 445:363-366 (1988). Taste cells show particular advantage for systems of the present invention because under suitable conditions such cells regenerate every few days by continuous division. Thus, prolonged growth of these cells when implanted is more readily sustained. Taste cells are also more accessible than beta cells. A sample of taste cells can be removed from a patient with only minor surgery, grown in culture to obtain a sufficient number of cells and then implanted. The ability to use a patient's own cells also reduced the likelihood of immunologic reactions to the implant. Taste cells can be isolated according to the methods of the publications cited above or by any other method which preserves the ability of the cells to respond to change in glucose concentration.

Alpha cells from the pancreas have also been shown to be sensitive to glucose concentration in the surrounding medium Sonerson et al., Diabetes 32:561-567 (1983). Transformed cell lines, such as the insulin producing line disclosed in U.S. Pat. No. 4,332,893, and hydridoma lines can also be used Any electrical activity associated with the response by alpha cells or transformed lines to glucose can be harnessed in practicing the present invention.

Many methods are known for implanting beta cells in human tissues. Altman et al., Diabetes 35:625-633 (1986); Ricordi et al., Diabetes 35:649-653 (1986); Brown et al., Diabetes 25:56-64 (1976); Schmidt et al., Diabetes 32:532-540 (1983). Other means for encapsulating living cells are disclosed in U.S. Pat. Nos. 4,663,286, 4,409,331, 4,352,883, 4,798,786, 4,689,293 and 4,353,888. Although the implanted cells of the present invention need not necessarily be encapsulated, any of these methods can be employed to produce an implantable capsule where such is used. The method of Altman et al. is preferred. The Altman capsule is a thin walled (about 100 microns thick) tube or elongated pellet made of a polyvinyl chloride acrylic copolymer, with a diameter of about 1 mm. These dimensions are preferred to maintain proper diffusion to all cells. The molecular-weight cut off of the Altman et al. capsule membrane was approximately 50,000. In preferred embodiments of the present invention, the cut off is less than 50,000 and most preferably between 1,000 and 10,000.

The capsule serves two basic functions. First, it serves as a barrier that prevents the cells from migrating away, while nutrients and waste products are free to diffuse through the capsule. Second, it serves to prevent antibodies and other large molecules from leaving or entering the capsule, for example, to prevent immunological reactions. The capsule also allows the use of glucose sensitive tumor cell lines as sensor cells which must be contained to prevent proliferation Any material which will provide these functions can be used to form capsules containing glucose sensitive cells.

In some embodiments, while not significantly interfering with production and detection of cellular electrical activity, the capsules are equipped with means for aiding detection of cellular electrical activity, such as electrodes or conducting bars that short-circuit the cell electric activity with the outside. The capsules are also preferrably implanted in clusters so as to ensure a detectable signal even if one or more capsules becomes disfunctional. The capsules may also contain means to fix them in the desired location or materials useful for determining the location of the capsules, such as radio-opaque materials.

Where the electrical activity is too low to be detected through the body surface without amplification or where the electrical activity is to be harnessed to drive an insulin pump, electrodes are placed on the inside of the capsule such that a potential difference can be measured across the electrodes which corresponds to the electrical activity of the cells inside the capsule. To prevent cell damage, these should be made from an inert metal, such as those commonly used in a variety of implants. See for example, "Cardiac Pacing and Physiology," Proceedings of the VIIIth World Symposium on Cardiac Pacing and Electrophysiology, Jerusalem, Israel, Jun. 2-11, 1987, ed. Belhassen et al., (Keterpress Enterprises, Jerusalem); IEE Trans. Biomed. Eng. 34:664–668 (1987); and J. Am. Coll. Cardiol. 11: 365-370 (1988). Since these electrodes are used for signal pickup only and not for electric stimulation, their functional lifetime should be practically indefinite. The electrodes are connected by insulated wires to an implanted signal pickup device for processing and amplification or to the insulin pump.

Figure 6A:
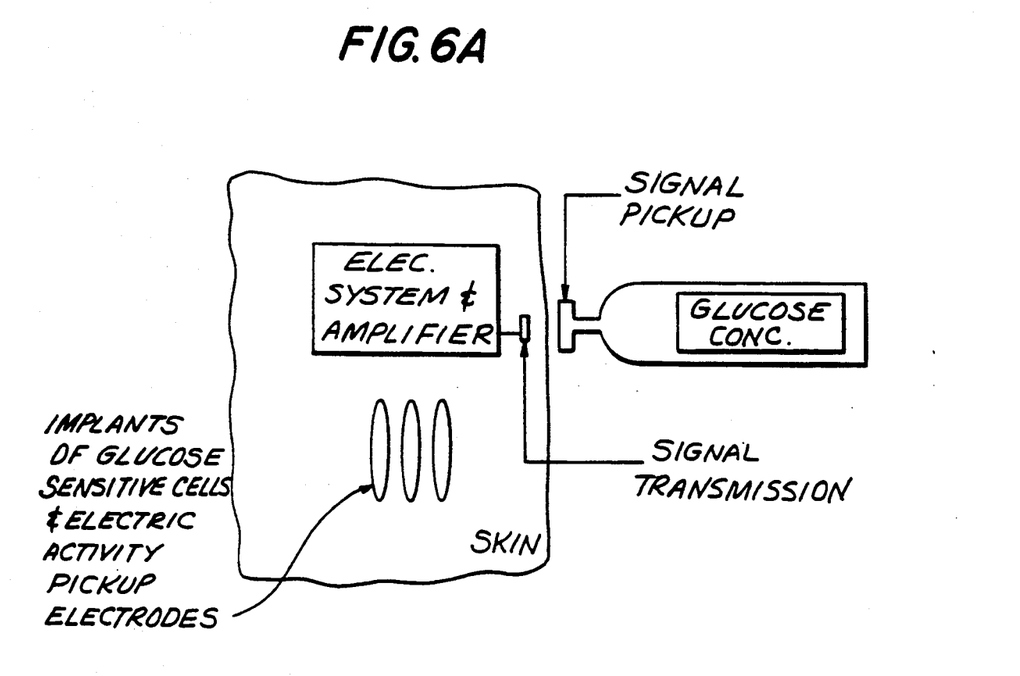
FIGS. 6A, 6B and 7 depict possible arrangements of the components of a system of the present invention with respect to the skin.
Figure 6B:
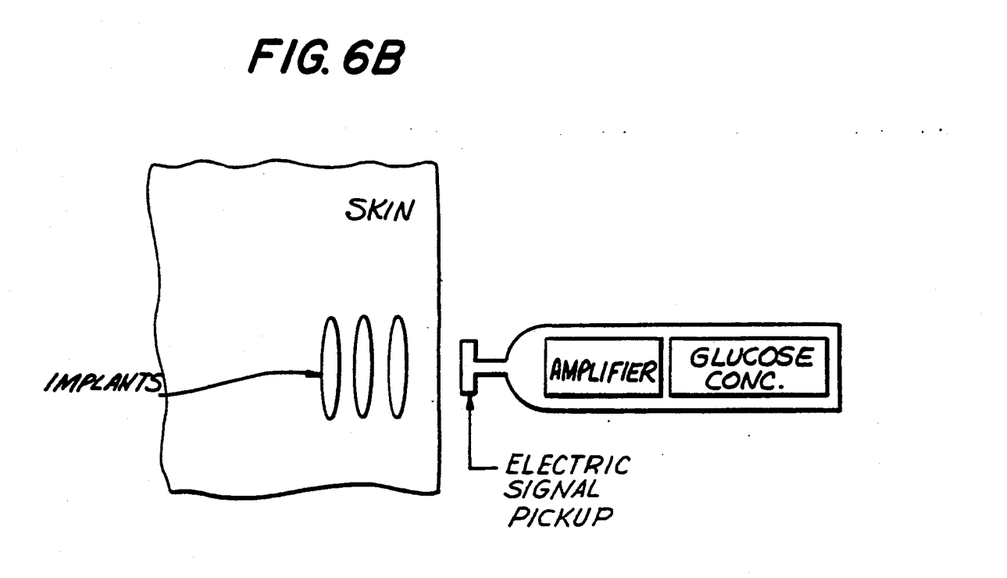

First, where the electrical activity of the implanted cells generates electric signals strong enough to be picked up from the external body surface by electrodes (as in EEG or ECG), the capsules are implanted near the surface of the skin where the skin is very thin and the location convenient. As shown in FIG. 6B, the signal is then detected by the external signal sensor. Alternatively, where the electrical activity is too small to be picked up by external means, electrodes are introduced into the capsule and connected to the implanted signal pickup device as shown in FIG. 6A. In this case the capsule implantation can be done anywhere in the body, for example, the peritoneal cavity where implantation is relatively easy and vascularization is adequate.

Figure 5:
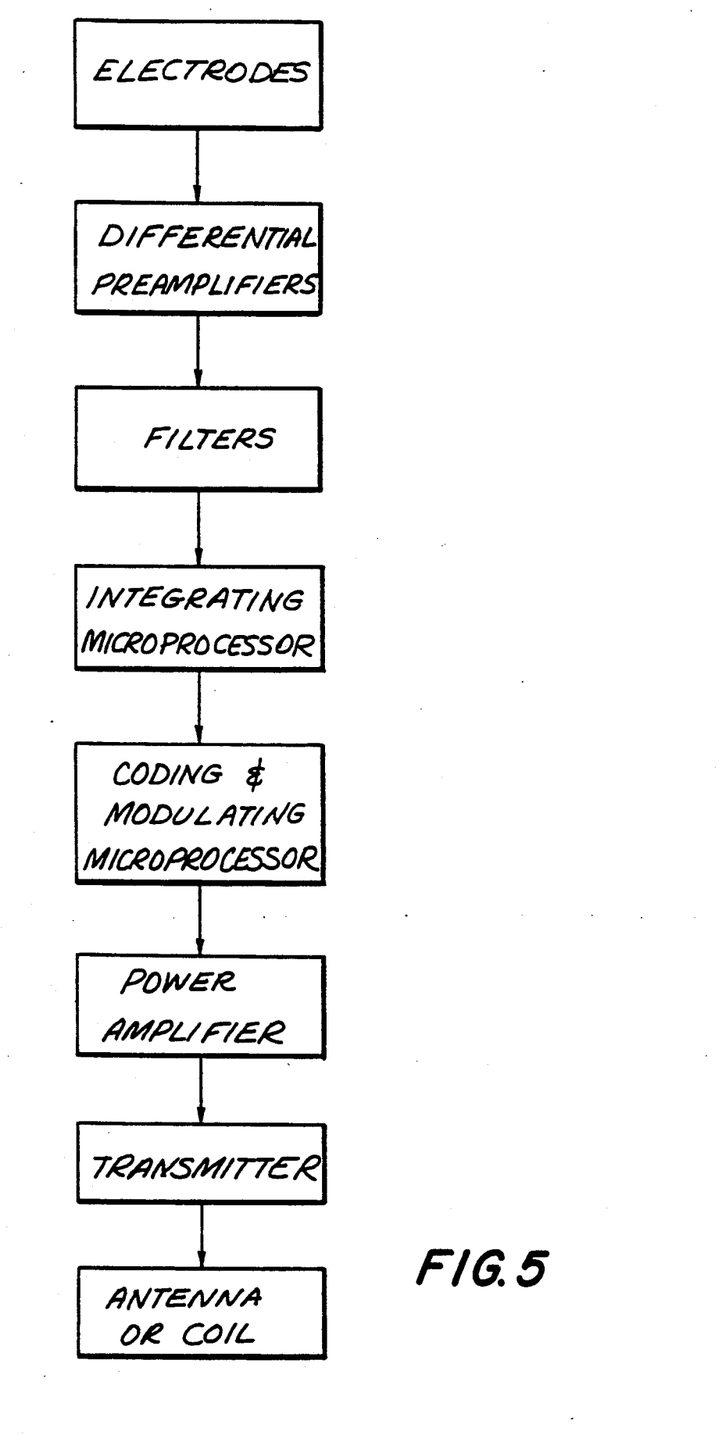

The basic components of the implanted signal pickup device are shown in FIG. 5. Basically, the device resembles implanted pacemakers in its external surface property. It can contain some or all of the following elements as necessary to provide a processed signal which is suitable for transmission or other desired use:

1. Inputs connected to the electrodes inside the implanted capsules.

2. A number of low noise, high input impedence differential preamplifiers corresponding to the number of capsules. Preferably, each capsule is connected to a single differential input amplifier.

3. Band pass filters at the outputs of the amplifiers. In certain embodiments, each amplifier may be connected through two filters, one designed to pass only the spikes (action potentials) while the other will pass only the very slow potential shifts associated with each burst of activity.

4. An integrating amplifier or microprocessor that sums up the output of all the preamplifiers.

5. A coding and modulating microprocessor that processes the summed signal so as to be best suitable for transmission across the skin, such as FM modulation. is connected to the transmitter that sends the processed signal through the skin.

There are two preferred alternative modes of transmission of the data from the internal implanted amplifier across the skin to the external sensor. In the first alternative, the amplifier is driven by low amplitude local currents by means of a pair of electrodes implanted under the skin. The electric field thus created is similar to those generated by the heart (such as in ECG measurement) and can be detected similarly by external electrodes. AC modulation of these currents will prevent local tissue stimulation, electrode polarization, and the like. In the second alternative, the output of the amplifier is fed, after proper modulation, to an induction coil or a coupling capacitive signal transferer. This coil generates an electromagnetic field that is picked up by a similar externally positioned coil. Other means for transmitting a signal across the tissue barrier will be apparent to skilled artisans and may be used in practicing the present invention.

Figure 4:
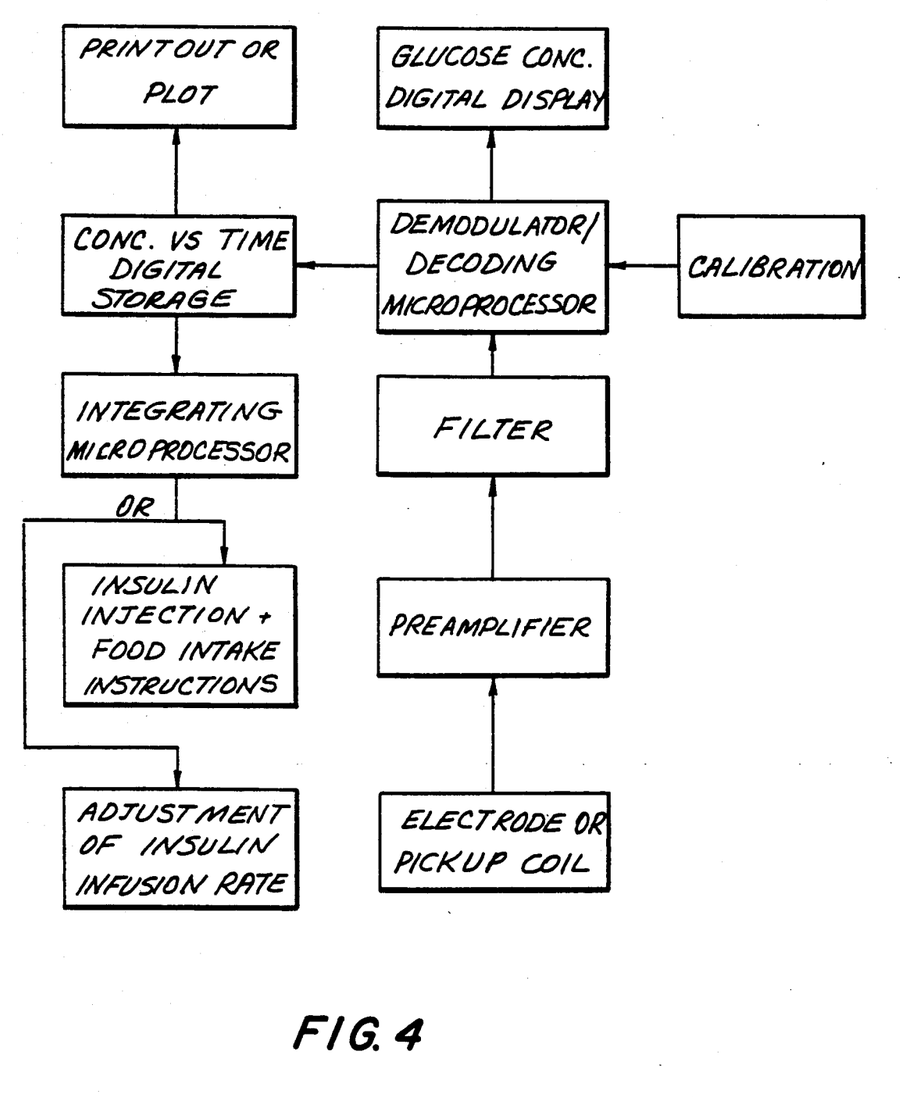
FIGS. 4 and 5 are schematic representations of the electrical components of systems of the present invention.

The signal from the capsules or the transmitter of the signal pickup device is detected by an external signal sensor. The basic components of the signal sensor are shown in FIGS. 4 and 6. In certain embodiments, the signal sensor can include one or more of the following elements:

1. A sensor, such as an electrode, coil or other means suited to detect the electrical or optical signal transmitted through the body surface.

2. A preamplifier connected to the sensors (which may not be necessary where the signal is already amplified before transmission across the skin barrier).

3. A filter for external noise reduction.

4. A demodulator - decoding microprocessor that separates the signals from their FM carrier or other modulation means when such a mode of transmission is used.

5. A signal processor that utilizes the appropriate algorithms and programmed information relating to glucose concentration to translate the transmitted signal into the corresponding glucose concentration.

The processed and decoded signal corresponding to determined glucose concentration is then passed on to means for outputting such information in the desired manner. For example, the concentration information can be presented as a digital readout in the form of a digital display on the probe itself or a display and printout in an associated device. A memory may be used to save the glucose values obtained during continuous or frequent glucose level monitoring. Such information including integretated glucose levels may also be used for determination of the correct amounts of insulin or insulin like drugs to be taken by the patient or determining patient diet. Such information can be displayed for patient use or as an input to an automated insulin infusion device.

A calibration system can also be associated with the system of the present invention. Since the exact dependency of electrical activity of the implanted cells on glucose concentration may vary with time, a means for recalibration of the system is provided Upon calibration the external device or probe is put into calibration mode. The current blood glucose level, as determined by a blood sample or other reliable means is fed manually (or automatically) to the calibration circuit that will reset the proper parameters of the concentration determining algorithms. A second glucose determination may be necessary at times to obtain two points on the calibration curve. Calibrations can be performed as frequently or infrequently as necessary to achieve and maintain the desired degree of accuracy in glucose level determination.

Figure 7:
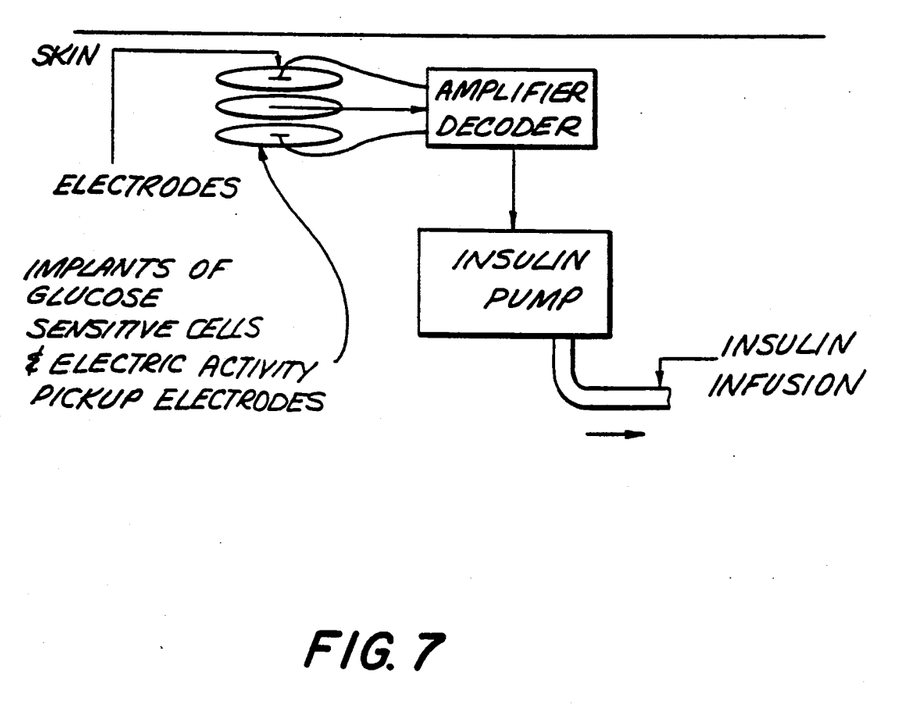

As shown in FIG. 7, in certain embodiments the processed signal is used to control an implanted insulin pump. By means of the controller the pump output is kept relatively consistent with the blood glucose levels thus allowing the pump to more closely mimic the human pancreas Most commercially available implantable pumps can be adapted for such use giving the pump similar properties to those of the beta cells.

Figure 8:
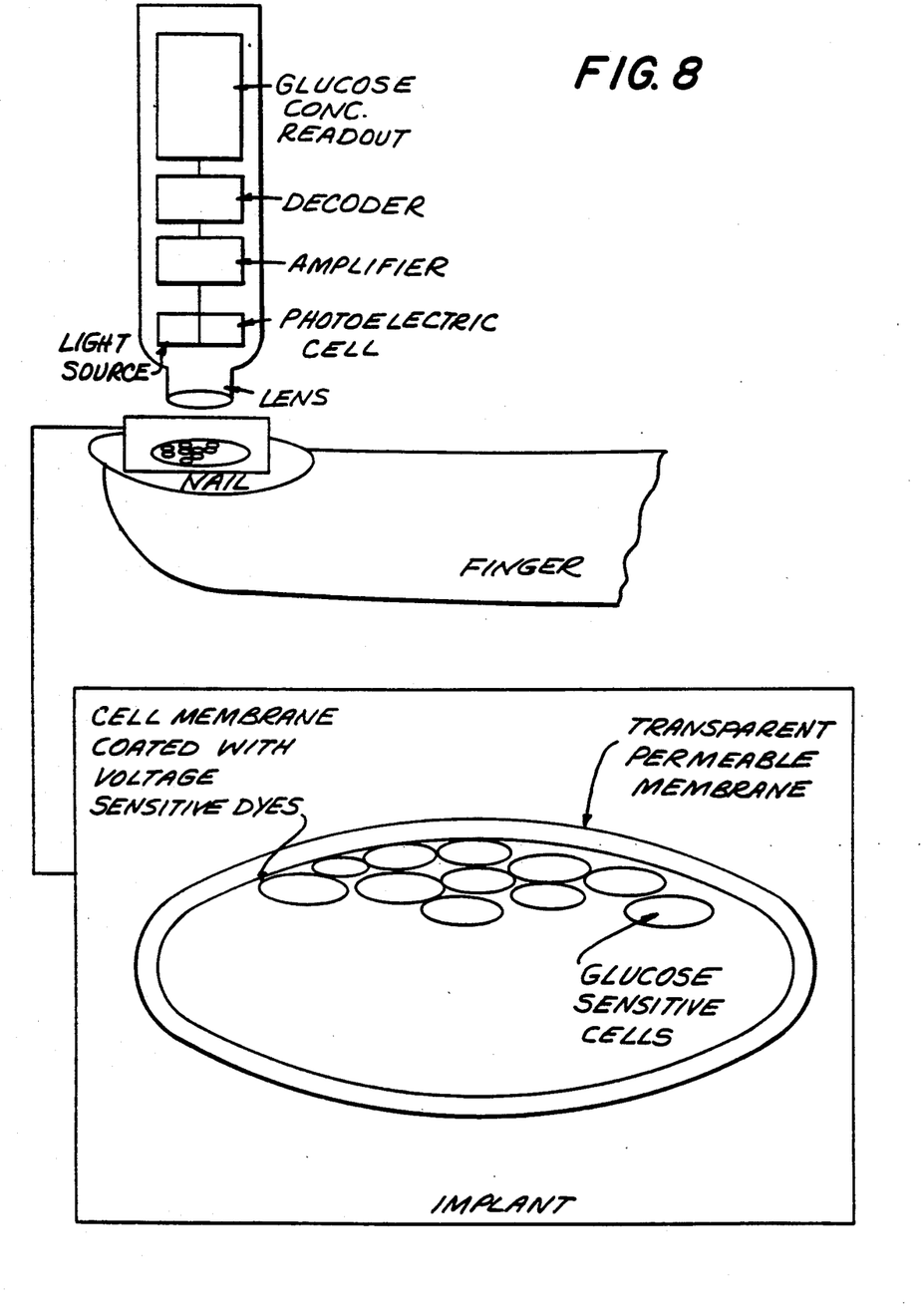
FIG. 8 depicts one embodiment of a system of the present invention that utilizes an optical signal.

An alternate embodiment of a system of the present invention converts the electrical activity of the glucose sensitive cells into an optical signal Direct changes in cell optical properties resulting from electrical activity can be measured as an optical signal Alternatively, biocompatible dyes which are sensitive to electric fields can be incorporated into the cell membranes and subjected to the membrane potential or electric field. Dyes useful for practicing this embodiment are disclosed in Grinvald et al., Physiol Rev. 68:1285-1366 (1988) and Gross et al., Biophys. J. 50:339-348 (1986). Other suitable dyes include those commercially available from Molecular Probes, Inc., Eugene, Oreg. The changes in the membrane potential induce changes in the optical properties of untreated cells or dyed cells, for example, in the optic density, fluorescence or birefringence of the cell membranes. Thus, the action potentials or electric spikes that the cells generate in response to glucose concentration induce changes in the optical properties of the cells (i.e., they generate optical signals). These signals are picked up by an implanted or external optic sensor. In certain embodiments, the cells are implanted such that a transparent body surface, such as thin skin layers or fingernails, separates them from the outside world. In optical signal embodiments, if a capsule is used, it must be constructed from a material through which the optical changes can be stimulated and measured (e.g., practically all thin plastics). One such implantation of cells is shown in FIG. 8. As shown, an external optical sensor monitors the cell activity and translates it into glucose concentration data. The external sensor can include a light source of the proper wavelength to excite the dyes or to be reflected from the cell surfaces and other components previously described for the external electrical signal sensor for processing, decoding and outputting the signal. Alternatively, the optical sensing components can be implanted such that an electrical signal, corresponding to the optical signal, is produced which can be detected or transmitted through the skin.

All of the literature and patent references identified herein are intended to be incorporated within the disclosure.

We claim:

1. A capsule implantable in a patient's body, said capsule comprising a thin walled tube or a pellet and being constituted of:
   (a) glucose-sensitive living animal cells capable of producing an electrical signal in response to the glucose concentration in the medium surrounding the capsule in the patient;
   (b) a membrane enclosing the cells, the membrane being impermeable to the cells and any antibodies and large molecules to prevent immunological reactions, and being permeable to nutrients for and waste products form the cells to maintain viability of the cells; and
   (c) electrodes within the membrane for measuring the potential difference corresponding to the electrical activity of the cells;
the dimensions of the capsule being sufficient to permit implantation in the patient's body and diffusion between the cells and the medium surrounding the capsule in the body.

2. A capsule as defined in claim 1 wherein the capsule comprises a thin walled tube.

3. A capsule as defined in claim 1 wherein the capsule comprises a pellet made of polyvinyl chloride acrylic copolymer.

4. A capsule as defined in claim 1 wherein the glucose-sensitive living animal cells are selected from the group consisting of beta cells, sensory cells, alpha cells, and combinations thereof.

5. A capsule as defined in claim 1 wherein the electrodes comprise an inert metal.

6. A capsule as defined in claim 1 wherein the membrane has a molecular weight not greater than about 50,000.

7. A capsule implantable in a patient's body, said capsule comprising a thin walled tube or a pellet and being constituted of:
   (a) glucose-sensitive living animal cells capable of producing an electrical signal in response to the glucose concentration in the medium surrounding the capsule in the patient;
   (b) a membrane enclosing the cells, the membrane being impermeable to the cells and any antibodies and large molecules to prevent immunological reactions, and being permeable to nutrients for and waste products from the cells to maintain viability of the cells; and
   (c) means for shorting out the interior of the capsule with respect to the exterior of the capsule such that electrical activity of the cells is dissipated in the exterior; the dimensions of the capsule being sufficient to permit implantation in the patient's body and diffusion between the cells and the medium surrounding the capsule in the body.

8. A capsule as defined in claim 7 wherein the capsule comprises a thin walled tube.

9. A capsule as defined in claim 7 wherein the capsule comprises a pellet made of polyvinyl chloride acrylic copolymer.

10. A capsule as defined in claim 7 wherein the glucose-sensitive living animal cells are selected from the group consisting of beta cells, sensory cells, alpha cells, and combinations thereof.

11. A capsule as defined in claim 7 wherein the membrane has a molecular weight not greater than about 50,000.

12. A capsule implantable in a patient's body, said capsule comprising a thin walled tube or a pellet and being constituted of:
   (a) glucose-sensitive living animal cells capable of producing an electrical signal in response to the glucose concentration in the medium surrounding the capsule in the patient; and
   (b) a membrane enclosing the cells, said membrane containing or being coated with at least one dye whose optical properties are changed by the electrical signal produced by said cells, the membrane being impermeable to the cells and any antibodies and large molecules to prevent immunological reactions, and being permeable to nutrients for and waste products from the cells to maintain viability of the cells; the dimensions of the capsule being sufficient to permit implantation in the patient's body and diffusion between the cells and the medium surrounding the capsule in the body.

13. A capsule as defined in claim 12 wherein the capsule comprises a thin walled tube.

14. A capsule as defined in claim 12 wherein the capsule comprises a pellet made of polyvinyl chloride acrylic copolymer.

15. A capsule as defined in claim 12 wherein the glucose-sensitive living animal cells are selected from the group consisting of beta cells, sensory cells, alpha cells, and combinations thereof.

16. A capsule as defined in claim 12 wherein the membrane has a molecular weight not greater than about 50,000.

* * * * *